US010444541B2

(12) United States Patent
Hyde et al.

(10) Patent No.: US 10,444,541 B2
(45) Date of Patent: Oct. 15, 2019

(54) SWITCHABLE LENS DEVICES, SYSTEMS, AND RELATED METHODS

(71) Applicant: Elwha LLC, Bellevue, WA (US)

(72) Inventors: Roderick A. Hyde, Redmond, WA (US); Melanie K. Kitzan, Bellevue, WA (US)

(73) Assignee: ELWHA LLC, Bellevue, WA (US)

( * ) Notice: Subject to any disclaimer, the term of this patent is extended or adjusted under 35 U.S.C. 154(b) by 200 days.

(21) Appl. No.: 15/267,526

(22) Filed: Sep. 16, 2016

(65) Prior Publication Data

US 2018/0078360 A1 Mar. 22, 2018

(51) Int. Cl.
*A61F 2/16* (2006.01)
*G02C 7/04* (2006.01)
*G02C 7/08* (2006.01)

(52) U.S. Cl.
CPC ............ *G02C 7/041* (2013.01); *A61F 2/1624* (2013.01); *G02C 7/04* (2013.01); *G02C 7/081* (2013.01); *A61F 2002/1681* (2013.01); *A61F 2230/0006* (2013.01); *A61F 2230/0008* (2013.01); *A61F 2250/0004* (2013.01)

(58) Field of Classification Search
CPC .......... G02C 7/041; G02C 7/04; G02C 7/081; A61F 2/1624; A61F 2002/1681; A61F 2250/0004
See application file for complete search history.

(56) References Cited

U.S. PATENT DOCUMENTS 6,851,805 B2 2/2005 Blum et al.
8,919,953 B1 12/2014 Ho
9,259,309 B2 2/2016 Fehr et al.
9,364,316 B1 * 6/2016 Kahook .................. A61F 2/167
9,877,824 B2 1/2018 Hyde et al.
2007/0121065 A1 5/2007 Cox et al.
2012/0140167 A1 * 6/2012 Blum .................... A61F 2/1624 351/159.34
2012/0281181 A1 * 11/2012 Chen ........................ G02C 7/04 351/159.03
2013/0261744 A1 10/2013 Gupta et al.
2016/0166200 A1 6/2016 Bal
2017/0020660 A1 1/2017 Hyde et al.

FOREIGN PATENT DOCUMENTS

WO WO 2015/105881 A1 7/2015

OTHER PUBLICATIONS

PCT International Search Report; International App. No. PCT/US2017/051346; dated Dec. 26, 2017; pp. 1-4.

* cited by examiner

*Primary Examiner* — David H Willse
*Assistant Examiner* — Tiffany P Shipmon
(74) *Attorney, Agent, or Firm* — Dorsey & Whitney LLP

(57) ABSTRACT

Embodiments disclosed herein are directed to switchable lens devices, systems, and methods that include determining relative tilt and/or vergence rotation of a subject's eyes and focusing one or more lenses based on the determined vergence rotation or a change therein. The switchable lens device can include one or more sensors configured to detect movement of at least one eye of the subject (e.g., to determine a least one of position, velocity, or acceleration of at least one eye of the subject). For example, the switchable lens device can include one or more acceleration sensors that can be operably coupled to or associated with a first eye or a second eye of the subject.

45 Claims, 6 Drawing Sheets

10
$\Phi_1$
100
110'
110
30
20

40
Φ2
100
110
20
110'
30

10
Φ1
100
110
20
110'
30

SWITCHABLE LENS DEVICES, SYSTEMS, AND RELATED METHODS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

BACKGROUND

Switchable lenses, such as intraocular lenses (IOLs) (e.g., pseudophakic IOLs, aphikic IOLs, or phakic IOLs (PIOLS)), contact lenses, and other lenses that are positionable before eyes of a subject can be used to correct the vision of the subject. For example, contact lenses and IOLs can include monofocal, multifocal, or accommodative configurations.

IOLs can include an optic element (e.g., lens) and haptic elements (e.g., arms or wings configured to aid in positioning the IOL). Such configurations can be limited to focusing either on near or far vision without selectively modifiable adjustment therebetween.

Therefore, manufacturers, users, and designers of IOLs continue to seek improved IOLs.

SUMMARY

Embodiments disclosed herein are directed to switchable lens devices such as IOL devices and systems, and methods that include determining relative tilt or vergence of a subject's eyes and focusing one or more lenses based on the determined vergence or a change therein. In an embodiment, the switchable lens device can include one or more sensors configured to detect movement of at least one eye of the subject (e.g., to determine at least one of position, velocity, or acceleration of at least on eye of the subject). For example, the switchable lens device can include one or more acceleration sensors that can be operably coupled to or associated with a first eye or a second eye of the subject. In an embodiment, a first acceleration sensor can be operably coupled to the first eye, and a second acceleration sensor can be operably coupled to the second eye of the subject.

Embodiments include a lens system that includes a first acceleration sensor operably coupleable to a first eye of a subject and a second acceleration sensor operably coupleable to a second eye of the subject. The lens system also includes at least one switchable lens device sized and configured to be placed in the first eye of the subject. The at least one switchable lens device includes at least one switchable lens configured to selectively switch between a first focal length and at least a second focal length that is less than the first focal length responsive to one or more switching signals. The lens system also includes a controller operably coupled to the first acceleration sensor and to the second acceleration sensor and operably coupled to the at least one switchable lens device. The controller includes control electrical circuitry configured to receive one or more first signals from the first acceleration sensor, receive one or more second signals from the second acceleration sensor, and generate the one or more switching signals for switching the at least one switchable lens from the first focal length to the second focal length or from the second focal length to the first focal length responsive at least partially to the one or more received first signals from the first acceleration sensor and from the second acceleration sensor.

Embodiment also includes a method of adjusting a focal length of one or more switchable lens devices. The method includes, at a controller, receiving one or more first signals from a first acceleration sensor operably coupleable to a first eye of a subject. The method also includes, at the controller, receiving one or more second signals from a second acceleration sensor operably coupleable to a second eye of a subject. Moreover, the method includes generating one or more switching signals for switching one or more switchable lenses from a first focal length to a second focal length or from the second focal length to the first focal length responsive at least partially to the one or more first signals from the first acceleration sensor and from the second acceleration sensor. The one or more switching signals correspond to a vergence between the first eye and a second eye of the subject.

Features from any of the disclosed embodiments can be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 2:
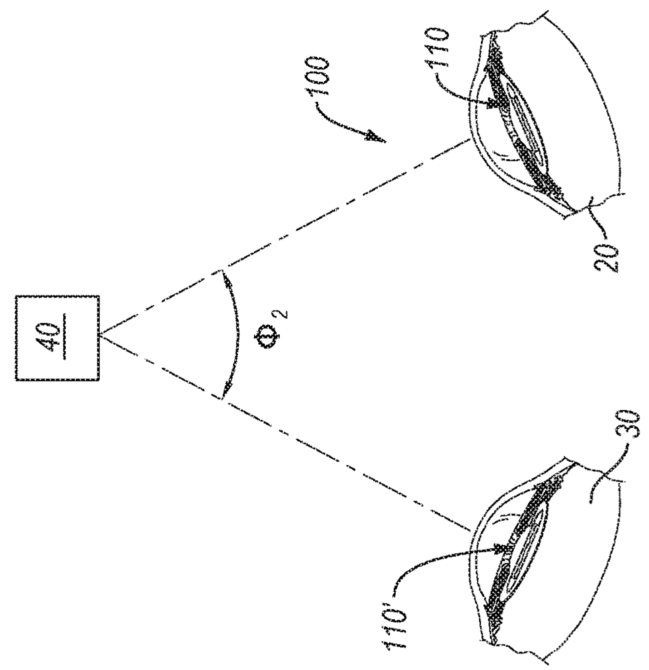
FIG. 2 is a schematic view of the subject's eyes of FIG. 1, with the eyes having a second vergence therebetween and are focused on a second object at a second distance from the subject that is less than the first distance, according to an embodiment.

Embodiments disclosed herein are directed to switchable lens devices such as IOL devices and systems, and methods that include determining relative tilt or vergence of a subject's eyes and focusing one or more lenses based on the determined vergence or a change therein. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented here.

In an embodiment, the switchable lens device can include one or more sensors configured to detect movement of at least one eye of the subject (e.g., to determine a least one of position, velocity, or acceleration of at least on eye of the subject). For example, the switchable lens device can include one or more acceleration sensors that can be operably coupled to or associated with a first eye or a second eye of the subject. In an embodiment, a first acceleration sensor can be operably coupled to the first eye, and a second acceleration sensor can be operably coupled to the second eye of the subject.

For example, the first and second acceleration sensors can move together with the corresponding first and second eyes of the subject, and can generate one or more signals that can correspond to the movement of the first and second eyes. Generally, the first and second acceleration sensors can include any suitable sensor capable of sensing or detecting acceleration. For example, acceleration sensors can include one or more of a MEMS accelerometer, a gyroscope, combinations or arrays thereof, etc. In an embodiment, the first acceleration sensor or the second acceleration sensor can be associated with or mechanically coupled to the switchable lens device. For example, the first acceleration sensor can be mechanically coupled to a first switchable lens of the switchable lens device, and the second acceleration sensor can be mechanically coupled to a second switchable lens of the switchable lens device.

In one or more embodiments, the switchable lens system can include at least one switchable lens device (e.g., an IOL device, a contact lens, etc.) that can be positioned in an eye of a subject. The acceleration sensor can be operably connected to the eye of the subject, such as to detect motion of the eye responsive to a vergence of the subject's eyes. Moreover, the acceleration sensor can be operably coupled to a controller that can direct the switchable lens to change an optical setting (e.g., a focal length) responsive to the output of the acceleration sensor, which is related to the vergence rotation. For example, as the eyes of the subject tilt or pivot, the accelerometer can detect a change in the velocity of the first eye or of the second eye (e.g., an acceleration of the first or second eye), and the detected changes in the velocity can be related to a vergence between the eyes of the subject.

In an embodiment, acceleration sensor can include a plurality of accelerometers that can be positioned in or operably coupled to the first eye or the second eye. For example, the plurality of accelerometers (e.g., an array of accelerometers) can determine acceleration of the first eye along multiple directions. Additionally, the plurality of accelerometers can determine acceleration of the second eye along multiple directions. In an embodiment, the controller can receive signals from the plurality of accelerometers and can determine angular acceleration or angular velocity of the first eye or of the second eye.

In an embodiment, the controller can compare signals received from the accelerometer sensor(s) to distinguish the vergence rotation from tilt rotation of the subject's eyes. For example, acceleration signals having a short duration and representative of higher acceleration of the eyes (e.g., compared to a selected or determined duration or acceleration values) can be associated with the change in vergence. Moreover, in an embodiment, the controller can determine a new focal length (e.g., a focal length to which to switch the switchable lens) responsive to the direction or the angular velocity or acceleration, as determined by the accelerometer (s). Hence, for example, the controller can generate one or more switching signals responsive at least in part to one or more signals received from the accelerometer(s).

In an embodiment, the switchable lens device can include one or more additional sensors (e.g., in addition to the acceleration sensors). For example, the switchable lens device can include one or more energy field sensors (e.g., magnetic or electric field sensors) and one or more field sources that can establish an identifiable field that can be sensed or detected by the field sensors. For example, the field can be an identifiable magnetic field established by a permanent or electromagnet. Furthermore, as discussed below in more detail, the field source (e.g., a magnetic field source) can be positioned in at least one eye of the subject. For example, the field source can be embedded in or mounted to a switchable lens device (e.g., IOL device, contact lens, etc.), that can be located in one of the subject's eye. Alternatively or additionally, the field source can be positioned near, but externally to one or both of the subject's eyes. In an embodiment, one or more sensors positioned in one or both eyes of the subject can detect a change in the identifiable field, or in a component thereof, during vergence rotation (e.g., as the vergence between the eyes changes), such as when the eyes converge or diverge. Hence, for example, the detected change in an identifiable magnetic field or a component thereof can correspond to a change in the vergence between the eyes.

As mentioned above, the switchable device system can include a controller. For example, the controller can be operably coupled to the field sensor and can receive detection output from the sensor. More specifically, the detection outputs from the sensor can be based on the detected change in the field or based on the one or more components thereof, which can be related to vergence rotation between the eyes of the subject. In an embodiment, the control can distinguish between vergence rotation of the eyes and co-tilt rotation of the eyes (e.g., when the eyes of the subject tilt in the same direction, such as to view an object located peripherally or to a side of the subject). As a consequence of such distinguishing, in such embodiments, each switchable lens can act independently of the other, reaching an accurate vergence determination (and hence an accurate focal length determination) on its own, without a need for communication between both of the switchable lenses so as to compare each switchable lens determined tilt with that of the other switchable lens in order to decide which portion of each switchable lens's tilt represents vergence and which represents co-tilt.

As discussed above, the switchable lens can be switchable between two or more focal lengths (e.g., a first focal length for distance vision and a second focal length for close-up vision). Moreover, the switchable lens device can include a single or multiple switchable lenses that can be directed or switched between two or more focal lengths by the controller. Moreover, the controller can be operably connected to the sensor(s) and can receive outputs therefrom, which can be related to the detected change in the field and, hence, to vergence rotation between the eyes. In an embodiment, the controller can switch or direct switching of the switchable lenses at least partially based on the outputs received from the sensor(s) or the one or more signals received from the accelerometer.

In an embodiment, the controller can compare the determination of change in vergence between the first eye and the second eye (e.g., whether the tilt of the first and second eye corresponds to a change in vergence), which is determined responsive to the one or more signals received from the accelerometer(s), to the determination of change in vergence, which is determined responsive to the one or more signals received from the sensors. For example, when the signals received from the accelerometer(s) and from the sensors indicate that the tilt of the subject's eyes corresponds to a change in vergence, the controller can determine that the eyes converged or diverged (e.g., based on the direction of movement of the eyes) or can generate a switching signal for switching the switchable lens from one focal length to another).

In an embodiment, the switchable lens systems disclosed herein can include one or more sensors configured to detect one or more physiological indicia of the subject. For example, the switchable lens system can include one or more sensors configured to detect glucose concentration (e.g., in the eye of the subject), eye pressure, heart rate, biological proteins present in the eye, or any other biological indicia. The one or more sensors can be operably coupled to the controller. The controller of the switchable lens system can be configured to transmit the measurements of the physical indicia to a remote source such as a computer, a cellular phone, or other electronic device. In an embodiment, the measured physical indicia may be used to determine the health of a subject or eye thereof, customize the operation of the switchable lens device to the particular subject, determine if the controller needs to be removed or adjusted, or determine if the focal adjustments of the controller are suitable for the subject. The electronic device may then transmit instructions to the controller to selectively control or otherwise adjust the functioning of the switchable lens system, such as controllably changing the focal length of the switchable lens device.

Figure 1:
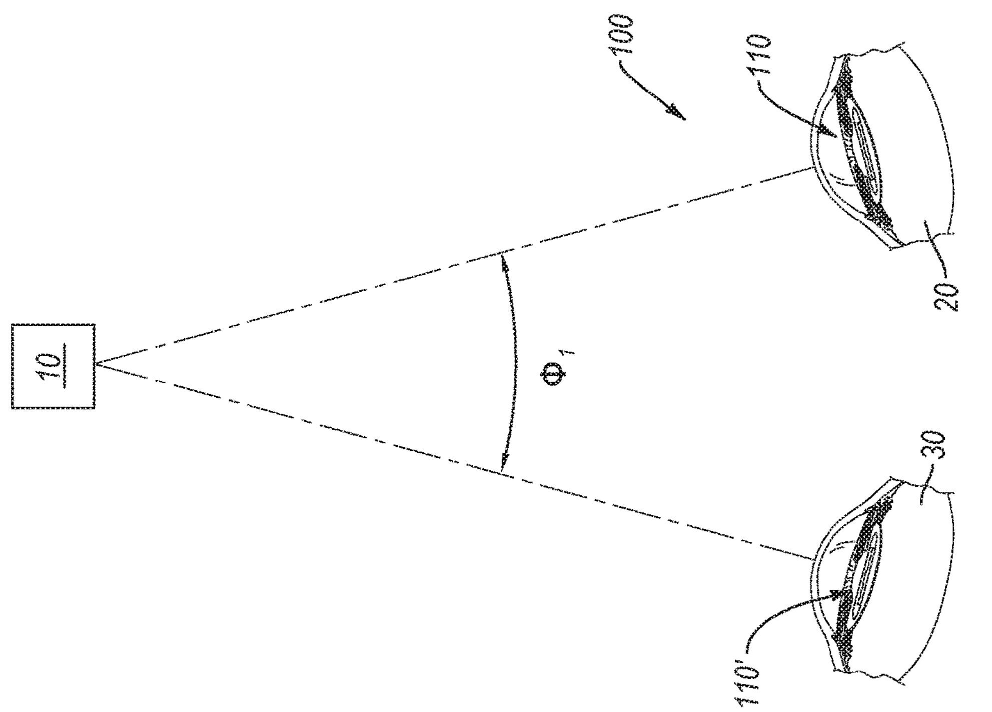
FIG. 1 is a schematic view of a subject's eyes having a first vergence therebetween and focused on a first object at a first distance from the subject, according to an embodiment.

FIG. 1 schematically illustrates eyes 20 and 30 of a subject focused on a first object 10 that is positioned at a first distance from the subject. In particular, when the eyes 20, 30 are focused on the first object 10, an angle between respective optical axes thereof can be at a vergence angle $\phi_1$. FIG. 1 also schematically illustrates a switchable lens system 100, according to an embodiment. For example, the switchable lens system 100 can include a first switchable lens device 110 positioned in a first eye 20 and a second switchable lens device 110' positioned in a second eye 30 of the subject. In the illustrated embodiment, the switchable lenses 110, 110' can be intraocular switchable lenses. Additionally or alternatively, the switchable lenses 110, 110' can be lenses that can be positionable externally to the subject's first and second eyes 20, 30 (e.g., contact lenses).

Generally, the first switchable lens device 110 or the second switchable lens device 110' can be configured to augment or correct visual deficiencies of the subject or to replace the lenses in the respective first eye 20 or second eye 30 of the subject (e.g., in cataract surgeries). It should be appreciated that, in one or more embodiments, the switchable lens system 100 can include only a single switchable lens (e.g., the first switchable lens device 110 or the second switchable lens device 110'), which can be positioned in the first eye 20 or in the second eye 30. The switchable lens devices 110 or 110' can be switched to or set at a first focal length, such that the light entering the eye from the distance of the first object 10 is focused on the retina of the respective eyes 20, 30, thereby focusing the eyes 20, 30 on the first object 10.

When the subject focuses on another object, such as an object that is closer to the subject than the first object 10, the object's eyes 20, 30 can tilt such as to converge, thereby changing the angle between the optical axes thereof. FIG. 2 schematically shows the subject's eyes 20, 30 focused on a second object 40, which is positioned at a second distance and closer to the subject than the first object 10 (FIG. 1). For example, when the eyes 20, 30 focus on the second object 40, the angle between the optical axis thereof can change to a second angle $\phi_2$. More specifically, as the eyes 20, 30 focus on the closer, second object 40, the eyes 20, 30 converge or in-tilt, such that the second angle $\phi_2$ defined by the respective optical axis thereof is greater than the first angle $\phi_1$.

In an embodiment, responsive to the changed tilt between the eyes 20, 30, the switchable lens devices 110 or 110' can be switched to the second focal length, which can be shorter than the first focal length. The switchable lens devices 110 or 110' can include one or more sensors that can sense or detect a change in an identifiable field (e.g., magnetic field) and can correlate that change to the change vergence rotation between the eyes 20, 30 (e.g., convergence to focus on a closer object or divergence to focus on a farther object). Similarly, as the subject attempts to focus eyes 20, 30 on an object at a distance that is greater than the distance to the second object 40 (e.g., on the first object 10 (FIG. 1)), the switchable lens devices 110 or 110' can be switched to the first focal length (longer than the second focal length).

Moreover, as described below in more detail, the switchable lens devices 110 or 110' can distinguish between vergence rotation from co-tilt rotation (e.g., when the eyes 20, 30 rotate in the same direction, such as to observe an object located peripherally from the user). As such, for example, the switchable lens device 110 or 110' can switch focal length responsive to detected vergence rotation. In an embodiment, the switchable lens devices 110 or 110' can maintain a previously set focal length during co-tilt of the eyes 20, 30.

Figure 3:
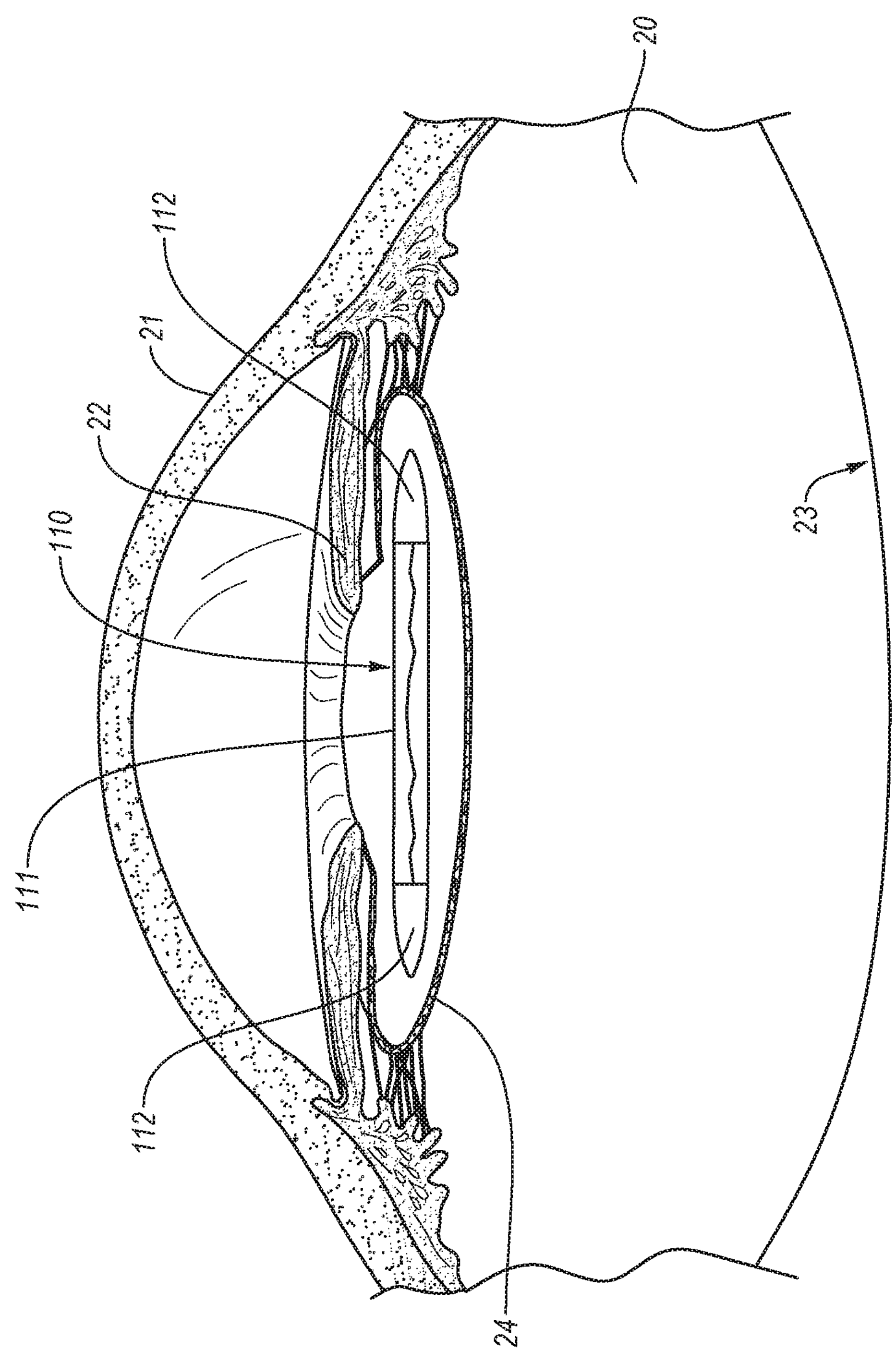
FIG. 3 is a schematic side, cross-sectional view of a subject's eye and a switchable lens device located in the eye, according to an embodiment.

As mentioned above, the switchable lens devices 110 or 110' can be located in the subject's eyes (e.g., in the eye 20 or in the eye 30). FIG. 3 is a schematic side, cross-sectional view of the eye 20 with the switchable lens device 110 implanted therein (e.g., the switchable lens device 110 can be an IOL device), according to an embodiment. It should be appreciated that, while the description herein is related to the switchable lens device 110 and to the corresponding eye 20 of the subject, the switchable lens device 110' or its location in the eye 30 (FIGS. 1-2) can have the same or similar configuration. Generally, the eye 20 includes a cornea 21, an iris 22, a natural lens, and a retina 23 therebehind. One or more switchable lens device 110 can be implanted in the eye 20. For example, the switchable lens device 110 can be implanted over the natural lens, in front of (e.g., in the anterior chamber) or behind the iris 22 (e.g., in the posterior chamber), or internal to the natural lens such as in a capsular bag 24 of the natural lens. In an embodiment, the natural lens can be absent from the eye 20 (e.g., the switchable lens device 110 can replace the natural lens and can be placed in the anterior chamber, the posterior chamber, or internal to the capsular bag that is used to contain the natural lens).

Generally, the switchable lens 110 can be any suitable lens that is configured to switch between at least two different optical settings (e.g., between two different focal lengths) responsive to one or more electrical inputs. Hence, for example, a controller can switch or direct switching of the switchable lens 110 among two or more optical settings. In an embodiment, the switchable lens 110 can be an electrically-modifiable diffractive lens, as described in more detail in U.S. application Ser. No. 14/807,673, the entire content of which is incorporated herein by this reference. Additionally or alternatively, the switchable lens 110 can be liquid crystal lens (e.g., a liquid crystal lens with an electrically tunable focal length).

Generally, as described below in more detail, the switchable lens device 110 can include a lens 111 and haptics 112 connected to or integrated with the lens 111. In an embodiment, the haptics 112 can be positioned on or secured to one or more structures in the eye 20, thereby positioning or securing the switchable lens device 110 in the eye 20. For example, the haptics 112 can be positioned on the ciliary body or muscles or in or on the capsular bag 24 of the natural lens. The lens 111 can be located laterally in the center of the eye 20 with the haptics 112 extending laterally therefrom. As mentioned above, the lens 111 of the switchable lens device 110 can be switched between two or more focal lengths, to focus light entering the eye from a selected distance on the retina 23 of the eye 20, thereby providing a focus on an object located at the selected focal length and augmenting or correcting the vision of the subject. Again, the switchable lens device 110 can include lenses that can be at least partially positionable externally to the subject's eyes, such as contact lenses. For example, the switchable lens 111 can be included in or can comprise a contact lens, the can be positionable near the subject's eye.

In an embodiment, the switchable lens device 110 can be substantially fixed within the eye 20 (e.g., the IOL device can be substantially immobile relative to the optical axis of the eye 20). As such, for example, movement of the eye 20 can result in a corresponding movement of the switchable lens device 110. In particular, as the eye 20 tilts or pivots in the eye socket, the switchable lens device 110 can correspondingly tilt or pivot together with the eye 20. Furthermore, one, some, or all of the elements or components of the switchable lens device 110 can have a predetermined orientation relative to the eye 20 or relative to the optical axis thereof, as described below in more detail.

Figure 4A:
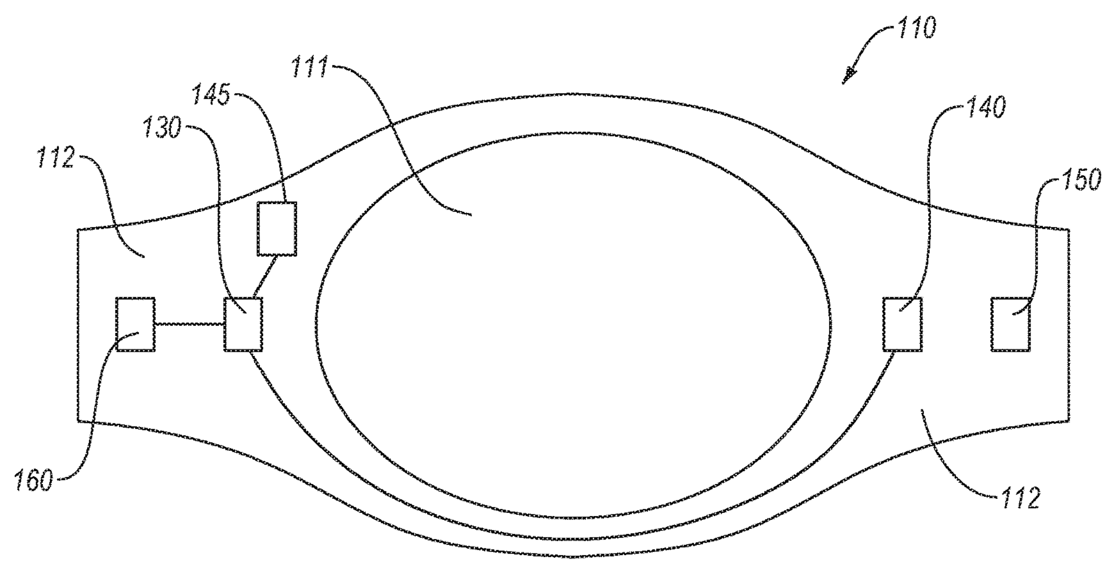
FIG. 4A is a top view of a switchable lens device, according to an embodiment.
Figure 4B:
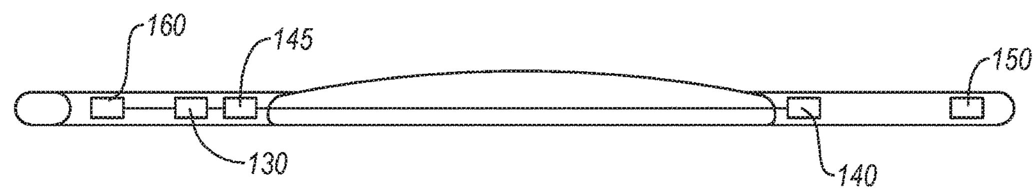
FIG. 4B is a side view of the switchable lens device of FIG. 4A.

FIGS. 4A and 4B illustrate switchable lens device 110, according to an embodiment. FIG. 4A is a top view of the switchable lens device 110, and FIG. 4B is a side view of the switchable lens device 110. The switchable lens device 110 can be configured to fit in or on one or more anatomical structures of the eye and can include the lens 111 and one or more haptics 112. As described above, the switchable lens device 110 can be an IOL device, a contact lens device, etc. For example, as will be apparent from the disclosure herein, a contact lens can be configured without the haptics 112.

As shown in FIG. 4A, in an embodiment, the switchable lens device 110 includes the lens 111. For example, the lens 111 can be configured to focus light onto the surface of the retina and can be substantially circular or elliptical. Furthermore, the lens 111 can be switchable between two or more optical settings, such as between two or more focal lengths (e.g., between three or more focal lengths).

In an embodiment, the lens 111 can include or can be configured as a switchable diffractive lens. Additionally or alternatively, the lens 111 can include or can be configured as a refractive lens that can have a selectively modifiable index of refraction and focal length (e.g., a variable focus refractive lens). In any embodiment, the lens 111 can be switched at least between the first focal length and at least a second focal length.

In an embodiment, a controller 130 can include control electrical circuitry that can be operably coupled to the lens 111 and can switch or direct switching of the lens 111 between two or more optical settings, such as between two or more focal lengths. For example, the control electrical circuitry of the controller can generate a switching signal and, responsive at least partially to the switching signal, the lens 111 can switch from a first optical setting, such as a first focal length, to a second optical setting, such as a second optical length. In an embodiment, the controller 130 can be positioned on or embedded in one or more portions of the switchable lens device 110. For example, a controller 130 can be mounted on or embedded in the haptics 112, in the lens 111 of the switchable lens device 110, or in another suitable portion of the switchable lens device 110.

Moreover, the controller 130 can receive a detection output from one or more sensors, such as from an acceleration sensor, field sensor, physiological characteristic sensor, etc. The detection output(s) from the sensor(s) can be related or correspond to the vergence rotation between the subject's eyes. At least partially based on the received detection output, the controller 130 can switch the lens 111 to a suitable or predetermined focal length.

For example, the controller 130 can be operably coupled to and can receive a detection outputs from a field sensor 140 or from an acceleration sensor 145. It should be appreciated that the field sensor 140 can include a single or multiple sensors that can detect presence or changes in a magnetic field. The acceleration sensor 145 can also include a single accelerometer, gyroscope, etc., or multiple accelerometers, gyroscopes, etc., (e.g., two or more of which can be arranged in an array). As described above, the field sensor 140, the acceleration sensor 145, the physiological characteristic sensor, etc., can be positioned on or embedded in one or more portions of the switchable lens device 110. For example, the field sensor 140 or the acceleration sensor 145 can be mounted on or embedded in the haptics 112 or in the lens 111 of the switchable lens device 110. Generally, the field sensor 140 can be any suitable sensor, such as sensor(s) suitable for detecting changes in the identifiable magnetic or electric field, which can correspond to vergence rotation of the eyes, as described below in more detail. As mentioned above, the switchable lens device 110 can include acceleration sensor 145, which can include any number of suitable sensors for detecting acceleration (or change in velocity or acceleration) of the subject's first or second eye.

Moreover, the field sensor 140, the acceleration sensor 145, or any additional sensors, such as physiological characteristics sensor, can be embedded in or mounted on the switchable lens device 110 (e.g., MEMS-based sensors that can be embedded in or mounted on one or more portions of the switchable lens device 110). Examples of suitable field sensors include Hall effect sensors, magnetoresistance sensors (e.g., AMR magnetometer, GMR magnetometer), induction coils, magneto-diodes, Lorentz force based sensors, an electron tunneling based sensor, or a MEMS compass. For example, the field sensor 140 can generate one or more detection outputs (e.g., a measurable change in voltage or resonant frequency) that can be related to or based on the changes in the position of an identifiable magnetic field, which can be related to the change in vergence between the subject's eyes. In an embodiment, the field sensor 140 can generate a signal that can include detection output of the field sensor 140. Examples of suitable acceleration sensors include MEMS-based accelerometers, MEMS-based gyroscopes (e.g., vibrating structure gyroscope), etc. For example, as described above, one or more signals received from the acceleration sensor 145 can be related to motion of the first or second eye of the subject and change in vergence therebetween.

The acceleration sensor 145 can be operably coupled or connected to the controller 130. As described above, the acceleration sensor 145 can be mechanically coupled to the switchable lens device 110 that can be operably connected or secured to the right or left eye of the subject. Hence, for example, the acceleration sensor 145 can generate one or more signals responsive to movement of the eye (e.g., responsive to the movement of the eye to which the switchable lens device 110 is connected), as the acceleration sensor 145 moves together with the eye.

In an embodiment, as the subject moves the eye together with the switchable lens device 110, the acceleration sensor 145 can generate one or more signals responsive to the motion of the eye, and the controller 130 can receive the signal(s) from the acceleration sensor 145. In particular, for example, responsive to the signal(s) received from the acceleration sensor 145, the controller 130 can determine acceleration of the eye (e.g., the rate of change of the eye's velocity and direction thereof), velocity of the eye (e.g., the rate of movement of the eye and movement direction). In an embodiment, the controller 130 can determine angular acceleration or velocity of the eye, at least partially responsive to the signal(s) received from the acceleration sensor 145 (e.g., at least partially based on the signals received from multiple accelerometers that can comprise the acceleration sensor 145, the controller 130 can determine the direction and magnitude of angular acceleration and velocity of the subject's eye).

In an embodiment, the switchable lens device 110 can optionally include a field source 150 (e.g., a magnetic field source), which can establish an identifiable magnetic field that can be detectable by an additional sensor that can be operably coupled to an additional controller. The field source 150 can be a dipole magnet (e.g., a permanent magnet, an electromagnet, combination of the foregoing, etc.) and can establish or generate a corresponding identifiable dipole magnetic field. Furthermore, the field source 150 can be mounted on or embedded in the switchable lens device 110. For example, the field source 150 can be embedded in the haptics 112 (as shown in FIG. 4B) or in the lens 111 of the switchable lens device 110.

In an embodiment, the field source 150 can be generally fixed in or stationary relative to the eye. Additionally or alternatively, the field source 150 can have a predetermine orientation relative to the eye or to the optical axis thereof. For example, the field source can be embedded within the switchable lens device 110 at a first predetermined orientation relative to the switchable lens device 110, and the switchable lens device 110 can be implanted within the eye at a second predetermined orientation relative to the eye. As such, for example, the identifiable field, such as an identifiable magnetic field can have a predetermined orientation relative to the eye or relative to the optical axis thereof.

Moreover, in an embodiment, the switchable lens device 110 can be positioned in the eye in a manner that movement of the eye results in a corresponding movement of the switchable lens device 110. Hence, for example, movement of the eye can produce a corresponding movement of the field source 150 and of the magnetic field established thereby. As such, a sensor detects the change in the established identifiable magnetic field, which can correspond to the movement of the identifiable magnetic field and of the eye (e.g., the movement of the eye can be tilting or pivoting of the eye that at least partially corresponds to a vergence rotation between the eyes). Methods, devices, and systems suitable for establishing one or more identifiable energy fields, measuring the energy fields, and determining change in the vergence rotation between the eyes based at least in part on the measurements are more fully described in U.S. patent application Ser. No. 14/807,719, the entire content of which is incorporated herein by this reference.

The switchable lens device(s) can be located in one or in both eyes of the subject. In an embodiment, a switchable lens device in the first eye can communicate with another switchable lens in the second eye, and vice versa (e.g., the switchable lens devices can be operably coupled together). For example, the switchable lens device in the second eye can send to the switchable lens device 110 in the first eye the detection output received from a first sensor in the switchable lens in the second eye, can send focal length determination, etc. In an embodiment, the switchable lens device 110 can include a communication device 160 (e.g., the controller 130 can be operably coupled to the communication device 160). The communication device 160 can be mounted on or embedded in the switchable lens device 110. For example, the communication device 160 can be embedded in the haptics 112 (as shown in FIG. 4B) or in the lens 111 of the switchable lens device 110.

The communication device 160 can be wireless (e.g., the communication device 160 can be a transmitter or a transceiver) or wired. For example, a wireless (e.g., RF-based or US-based) connection can be established between the communication device 160 and another or additional communication device. Alternatively, the communication device 160 and another communication device can have a wired connection therebetween. For example, an electrical conductor connecting the communication device 160 and another communication device can be implanted in or near the eyes of the subject. In any embodiment, the communication device 160 can be operably coupled to the additional communication device, such as to send data therebetween.

In an embodiment, one or more of the controller 130, the field sensor 140, the acceleration sensor 145, the field source 150, or communication device 160 can be operably coupled or connected to a power source. For example, the power source can include a rechargeable energy storage device or battery (not shown) that can be mounted on or embedded in the switchable lens device 110. The battery can be wirelessly recharged (e.g., a wireless or inductive charger can recharge the battery). In an embodiment, the battery can be operably connected to a photovoltaic cell that can be mounted on or embedded in the switchable lens device 110. Alternatively or additionally, the battery can be operably connected or coupled to a charge port that can be configured to accept a charging device. In any event, the power source can power one or more of the controller 130, field sensor 140, field source 150, or communication device 160.

In an embodiment, the power source may include a parasitic power device, such as an induction coil, one or more photocells, thermoelectric device, or any other device configured to harvest energy from a subject or the environment. For example, the induction coil can include a channel having a magnet therein, the channel passing the induction coil upon movement of the subject (e.g., eye-movement or blinking). In an embodiment, an induction coil can be disposed in the eye of a subject (e.g., in or adjacent to the switchable lens) and a corresponding magnet may be positioned on an adjacent part of the subject (e.g., an eyelid or bridge of the nose) whereby movement of the eye or eyelid can cause a current in the induction coil.

Again, while the switchable lens device 110 is described as including the controller 130, the field sensor 140, the acceleration sensor 145, the field source 150, and communication device 160, configurations of the switchable lens device 110 can vary from one embodiment to the next. In particular, for example, the switchable lens device 110 can include only the controller 130 and the acceleration sensor 145 that can detect a change in the position, velocity, or acceleration of the subject's first or second eye). Also, one of the switchable lens device (e.g., of a switchable lens system) can include only the acceleration sensor 145, the field source 150, and the controller 130, which the other switchable lens device can include the field sensor 140 that can be operably coupled to the controller 130.

As described above, the switchable lens system can include a single switchable lens device or multiple switchable lens devices (e.g., a switchable lens device can be located in one or in both eyes of the subject). Generally, the switchable lens devices of the switchable lens system can be similar to or the same as the switchable lens device 110. It should be appreciated, however, that any of the switchable lens devices included in the switchable lens systems described herein can include or can be operably coupled to any number of controllers, sensors, field sources, communication devices, or combinations thereof, which can be similar to or the same as the controller 130, field sensor 140, acceleration sensor 145, field source 150, and communication device 160. It should be appreciated that the field source 150 or the field sensor 140 are optional for the switchable lens device 110 or for operation thereof or of the controller 130.

Figure 5A:
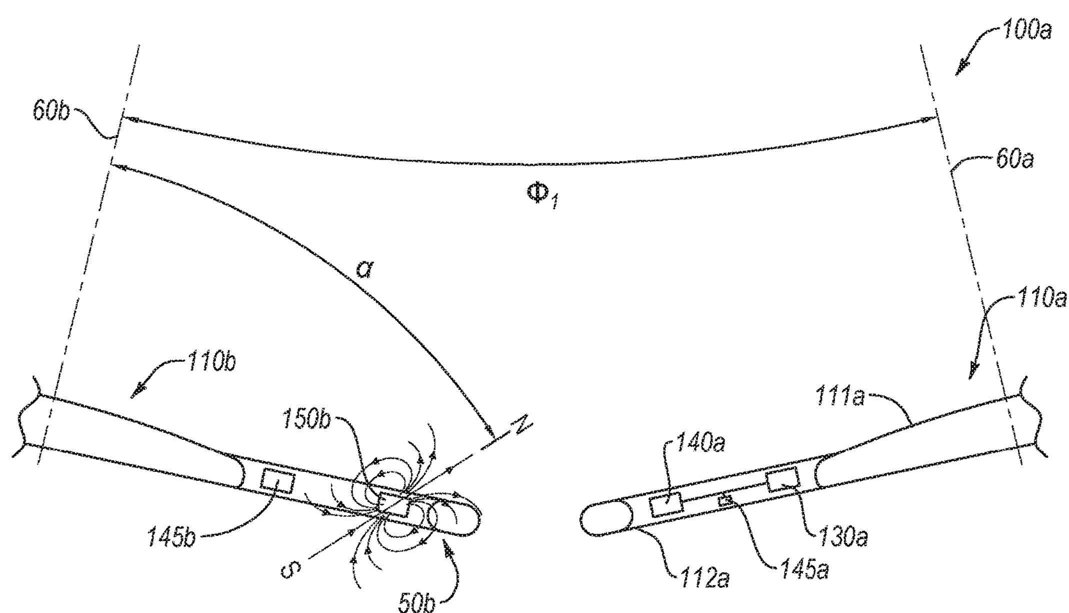
FIG. 5A is a schematic top view of a switchable lens system that includes two switchable lens devices oriented by the subject's eyes at a first vergence therebetween, according to an embodiment.
Figure 5B:
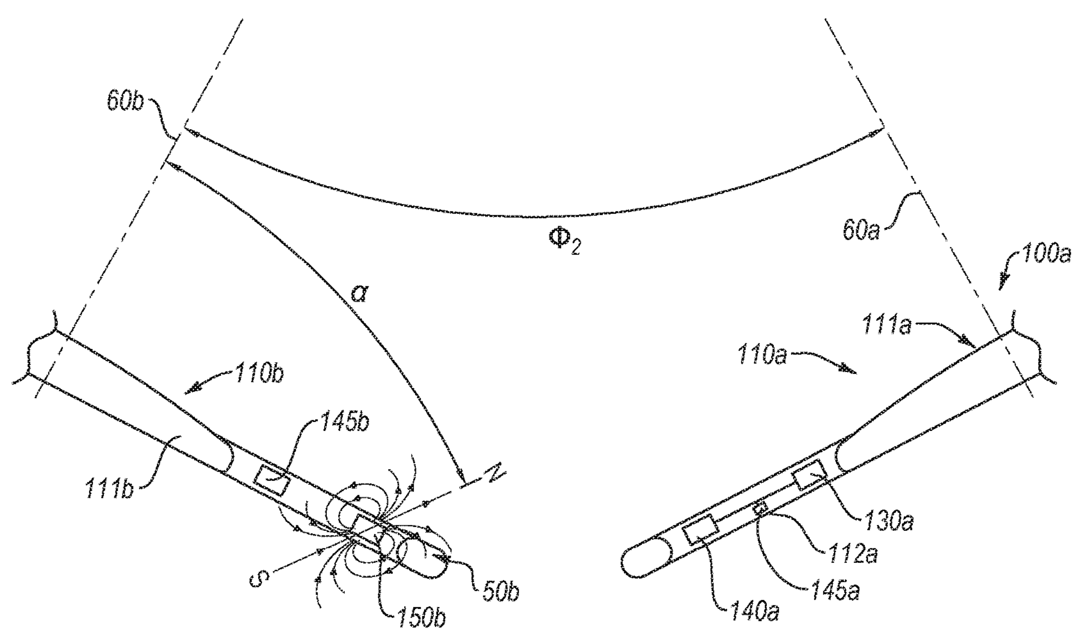
FIG. 5B is a schematic top view of the switchable lens system of FIG. 5A in which the switchable lens devices are oriented by the subject's eyes at a second vergence therebetween, according to an embodiment.

In an embodiment, the switchable lens system can include a single switchable lens device 110 or can include multiple switchable lens devices that can be similar to or the same as the switchable lens device 110 (e.g., the switchable lens system 100 (FIGS. 1-2)). FIGS. 5A-5B schematically illustrate a switchable lens system 100*a* that includes a first switchable lens device 110*a* in the first or right eye (not shown), and a second switchable lens device 110*b* in the second or left eye (not shown), according to an embodiment. It should be appreciated that designations, first eye/right eye and second eye/left eye are used for ease of description only and should not be read as limiting (e.g., the first switchable lens device 110*a* can be positioned in the second or left eye and the second switchable lens device 110*b* can be positioned in the first or right eye). Except as otherwise described herein, any of the first switchable lens device 110*a*, second switchable lens device 110*b*, and their elements and components can be similar to or the same as the switchable lens devices 110, 110' (FIGS. 1-4B) and their corresponding elements and components.

FIG. 5A illustrates the first switchable lens device 110*a* and the second switchable lens device 110*b*, with respective first and second optical axes 60*a* and 60*b* of the first and second eyes oriented to define a first angle $\phi_1$ therebetween, at which the eyes are focused on first object at first distance from the subject. FIG. 5B shows the first and second eye focused on a second object that is closer than the first object, and the first and second optical axes 60*a*, 60*b* define a second angle $\phi_2$ that is smaller than the first angle $\phi_1$.

In an embodiment, the first switchable lens device 110*a* includes a first field sensor 140*a* and a first acceleration sensor 145*a* operably coupled to a controller 130*a* including control electrical circuitry (e.g., the first field sensor 140*a*, first acceleration sensor 145*a*, or controller 130*a* can be embedded in one or more portions of the first switchable lens device 110*a*, such as in the haptics 112*a* of the first switchable lens device 110*a*). Moreover, the controller 130*a* can be operably coupled to first lens 111*a* of the first switchable lens device 110*a*, such as to switch or direct switching of the focal length of the first lens 111*a* at least between two different focal lengths.

As described above, the first switchable lens device 110*a* can include a first acceleration sensor 145*a*, and the second switchable lens device 110*b* can include a second acceleration sensor 145*b*. Moreover, the first and second switchable lens devices 110*a*, 110*b* can be operably associated with the respective first and second eyes of the subject, such that movement of the first eye correspondingly moves the first switchable lens device 110*a*, and movement of the second eye moves the second switchable lens device 110*b*. Hence, as the subject moves or tilts the eyes toward or away from each other, to change the vergence therebetween, the first and second acceleration sensors 145*a*, 145*b* of the first and second switchable lens devices 110*a*, 110*b* can detect the movement of the eyes.

Moreover, the one or more signals received by the controller 130 from one or more acceleration sensors (e.g., from the first and second acceleration sensors 145*a*, 145*b*) can be related to or indicative of acceleration of the first eye and of the second eye. Hence, the controller 130*a* can determine the velocity of the first eye by integrating the function of the acceleration (e.g., over time, to determine velocity at a specific time), which can be generated responsive to the one or more signals received from the first and second acceleration sensors 145_a_, 145_b_. Also, the controller 130 can determine the position or change in position of the first eye and second eye (e.g., by integrating over time the function of velocity).

In an embodiment, as described above, the controller 130_a_ can determine a change in vergence between the eyes based on the determined acceleration, velocity, or position (or change in position) of each of the eyes. Additionally, the controller 130_a_ can distinguish the change in vergence between the first eye and second eye and tilt of the first eye or the second eye. For example, when tilted, the optical axes 60_a_, 60_b_ of the first and second eyes can be oriented substantially parallel to each other, while when focused on an object in front of the subject, the optical axes 60_a_, 60_b_ can be oriented at non parallel angles (e.g., as shown in FIGS. 5A-5B), where the first and second angles $\phi_1$, $\phi_2$ are non-zero angles. Hence, for example, the controller 130_a_ can determine the first and second angles $\phi_1$, $\phi_2$ based on the change in one or more of the acceleration, velocity, or angular position or orientation of the first and second eyes. Moreover, the controller 130_a_ can determine the first and second angles $\phi_1$, $\phi_2$ based on the change the field or one or more of the components thereof, as detected by the field sensor 140_a_ or 140_b_.

In an embodiment, the controller 130_a_ can determine one or more of a difference in angular position, a difference in angular velocity, or a difference in angular acceleration between the first eye and the second eye based on the one or more first signals received from the first acceleration sensor 145_a_ and one or more second signals received from the second acceleration sensor 145_b_. For example, the controller 130_a_ can include or can be operably connected to a data table that can correlate one or more of a difference in angular position, a difference in angular velocity, or a difference in angular acceleration between the first eye and the second eye with the vergence between the eyes. For example, the subject can train the controller 130_a_ or generate the table responsive to prompts from the controller 130_a_.

In an embodiment, the controller 130_a_ can receive one or more signals from the first and second acceleration sensors 145_a_, 145_b_, determine one or more of a difference in angular position, a difference in angular velocity, or a difference in angular acceleration between the first eye and the second eye, and prompt user for input identifying the vergence or tilt of the eyes; the input can be stored in the table and correlated with the signals received from the first and second acceleration sensors 145_a_, 145_b_. Additionally or alternatively, the controller 130_a_ can receive one or more signals from the first and second acceleration sensors 145_a_, 145_b_, determine one or more of a change difference in angular position, a change difference in angular velocity, or a change difference in angular acceleration between the first eye and the second eye, and prompt user for input identifying the vergence or tilt of the eyes; the input can be stored in the table and correlated with the change in signals received from the first and second accelerometers 145_a_, 145_b_ or with the changes in the acceleration, velocity, or position.

In an embodiment, the controller 130_a_ can receive one or more signals from the first and second acceleration sensors 145_a_, 145_b_ and can generate one or more switching signals for switching the lenses 111_a_ or 111_b_ from a first optical setting to a second optical setting. For example, the lens 111_a_ or lens 111_b_ can have a first focal length at the first optical setting and a second focal length at the second optical setting.

In an embodiment, multiple switchable lenses can be switched or controlled by a single controller, such as the controller 130_a_. Additionally or alternatively, each of the multiple lenses can include a controller and the respective controllers can be operably coupled to each other (e.g., via hardwired connection, wireless connection, etc.), such that a first controller receives one or more signals from a second controller and vice versa. For example, first controller can receive signals from second controller; the signals can be related to the acceleration or velocity of the second eye (e.g., based on the one or more signals received at the second controller from the acceleration sensor). Moreover, multiple controllers, each of which can include a respective electrical circuitry, can operate collectively as a single controller that can generate one or more switching signals for a first lens in the first eye of the subject or for the second lens in the second eye of the subject.

It should be appreciated that the controller 130_a_ or one or more portions thereof can be located at any number of suitable locations (e.g., relative to the first and second switchable lens devices 110_a_, 110_b_. In an embodiment, the controller 130_a_ can be located remotely from the at least one or from both of the first and second switchable lenses 111_a_, 111_b_. For example, a portion of the controller 130_a_ can be located or included in a personal electronic device (e.g., a smart phone or the like).

Generally, the first and second acceleration sensors 145_a_, 145_b_ can be operably coupled to the controller 130_a_ with any number of suitable connections. For example, the acceleration sensor 145_a_ or 145_b_ can be operably coupled to the controller 130_a_ via at least one of a radio frequency connection, an optical transmission connection, an ultrasonic connection, or an electrical-conductor connection. Additionally or alternatively, the first or second acceleration sensor 145_a_, 145_b_ can be coupled to the controller 130_a_ by a hardwired connection.

As described above, the controller 130 can generate one or more switching signals to switch or direct switching of the lens 111 from a first optical setting to a second optical setting, or vice versa. In an embodiment, the controller 130 can generate the one or more switching signals responsive to the one or more signals received from first acceleration sensor 145_a_ that detected motion of the first eye or from the one or more signals received from second acceleration sensor 145_b_ that detected motion of the second eye. That is, for example, the controller 130 can generate the one or more switching signals responsive to the detected change in vergence between the first eye and second eye, and detection of the change in vergence between the eyes can be based on determined acceleration or velocity of the eyes (e.g., angular acceleration or velocity determined by the controller 130 based on one or more signals received from the acceleration sensor(s)).

In an embodiment, at least one acceleration sensor can be located outside of the first and second switchable lens devices 110_a_, 110_b_. For example, at least one acceleration sensor can be positioned remotely from the subject's first and second eyes. At least one acceleration sensor that is positioned externally to the first and second eyes of the subject can be operably coupled to the controller 130_a_; hence, in an embodiment, one or more signals received by the controller 130_a_ from such sensor(s) can be associated with the general movement of the subject and not with the movement of the subject's first or second eye (e.g., can be associated with movement of the subject's body or head).

In an embodiment, the controller 130_a_ can compare the signals or acceleration determined from the remote acceleration sensor(s), which are positioned remotely of the subject's eyes, to the signals or acceleration determined from the first or second accelerations sensor 145*a*, 145*b*. For example, the controller 130*a* can filter out at least some of the noise that may be present in the signals received from the first and second acceleration sensors 145*a*, 145*b* (e.g., the controller 130*a* can subtract the acceleration determined from the remote acceleration sensors from the acceleration determined from one or more of the acceleration sensors 145*a*, 145*b*). In an embodiment, the controller 130*a* can filter out one or more signals from the first and second acceleration sensors 145*a*, 145*b*, such as signals that may correspond to general vibration of one or more portions of the sensors (e.g., noise from vibration of the mass of a MEMS sensor that may occur without movement of the subject or subject's eyes) and can filter out signals resulting from movement of the subject (e.g., walking, driving, etc.).

In an embodiment, the controller 130*a* can include or can be operably connected to a storage that includes or stores signal samples corresponding to signal noise. For example, the controller 130*a* can receive one or more signals from the first and second acceleration sensors 145*a*, 145*b* while the subject is not moving the eye and standing still, while the subject is walking, while the subject is driving, etc. (e.g., to identify noise signals received from the first and second acceleration sensors 145*a*, 145*b* under different conditions when the subject is not moving the eyes). Hence, the controller 130*a* can filter out or ignore one or more signals or portions of the signals received from the acceleration sensors 145*a*, 145*b*, which correspond or similar to the noise signals previously received by the controller 130*a* (e.g., during calibration of the controller 130*a*). Moreover, during use of the switchable lens system 100*a*, the noise characteristics of the first and second acceleration sensors 145*a*, 145*b* can change over time. In some embodiments, the controller 130*a* can be configured to retest or rest the stored noise signals. For example, to calibrate or recalibrate the controller 130*a* or the first or second acceleration sensor 145*a*, 145*b*, the subject can periodically perform various activities without moving eyes and provide feedback or input to the controller 130*a* that can correlate various conditions of the subject, such as walking, sitting, driving, etc., with noise signals received from the first and second acceleration sensors 145*a*, 145*b*.

In an embodiment, the controller 130*a* can reject or filter out signals related to or indicative of up and down movements of the eyes. For example, based on one or more received signals or inputs (e.g., based on signals received from the acceleration sensors 145*a*, 145*b*), the controller 130*a* can determine orientation of the subject's head relative to gravitational vector. Moreover, as described herein, based on the signals received from the acceleration sensors 145*a*, 145*b*, the controller 130*a* can determine direction of movement of the subject's eyes relative to the head of the subject. For example, the controller 130*a* can determine movement of the subject's eyes relative to the gravitational vector and correlate the determined movement to the orientation of the subject's head relative to the gravitational vector to determine the movement of the eyes relative to the head. Hence, for example, the controller 130*a* can filter out signals from the acceleration sensors 145*a*, 145*b*, which correspond to up and down movement of the eyes relative to the subject's head, such as toward the forehead and toward the nose (e.g., irrespective of the orientation of the subject's head), or up or down movement of the subject's head.

In some embodiments, the controller 130*a* can be configured to differentiate at least one noise signal and at least one detection signal by comparing magnitude of a signal to the magnitude of a second signal and by identifying the first signal as the at least one noise signal. For example, both the first and second signals can be received from the same acceleration sensor (e.g., from the first acceleration sensor 145*a* or from the second sensor 145*b*). In an embodiment, the controller 130*a* can filter out signals below a certain magnitude threshold. For example, the controller 130*a* can determine an average signal level while the subject is not moving the eyes and filter out or subtract signals below the threshold of the average signal level.

As described above, at least one of the switchable lens devices can include an energy field sensor (e.g., a sensor configured to detect a change in a magnetic or electric field). Moreover, in some embodiments, at least one of the switchable lens devices can include a field source that can generate an identifiable energy field (e.g., a magnetic field) that can be detected by the energy field sensor. In the illustrated embodiment, the second switchable lens device 110*b* can include a magnetic field source 150*b* mounted thereon or embedded therein.

The magnetic field source 150*b* can establish an identifiable magnetic field 50*b* that can be sensed by the first field sensor 140*a*. More specifically, for example, the first field sensor 140*a* can detect the change in orientation or location of the identifiable magnetic field 50*b*. It should be also appreciated that the magnetic field source 50*b* can be positioned or secured in the subject's second eye without the second switchable lens device 110*b* (e.g., the magnetic field source 50*b* can be implanted in the eye, such as in the sclera of the eye). In any event, in one or more embodiments, the magnetic field source 150*b* can move and tilt together with the second eye (correspondingly moving the identifiable magnetic field 50*b*), and the first field sensor 140*a* can detect the change in the orientation or location of the identifiable magnetic field 50*b*. It should be also appreciated that any of the elements or components described herein as included in one or more switchable lens devices can be directly implanted in the eye or secured to the eye, without implanting or otherwise associating a switchable lens device in that eye (e.g., a controller, an acceleration sensor, a field source, a field sensor, etc., can be implanted directly in the eye).

In an embodiment, the controller 130*a* can be configured to correlate the detected change in the identifiable magnetic field 50*b* with the vergence rotation between the eyes. For example, the first field sensor 140*a* can generate a detection output that can correspond to a change at least partially corresponding to the vergence rotation by detecting a changed component of the identifiable magnetic field, which can be in a direction substantially perpendicular to a direction of a dominant component of the identifiable magnetic field. Furthermore, the detection output can be received by the controller 130*a*, and based on the detection output, the controller 130*a* can determine the vergence rotation between the eyes.

In an embodiment, at least partially based on or from the determined vergence rotation, the controller 130*a* can determine an apparent or estimated object distance (e.g., the distance from the subject to the object on which the subject's eyes are attempting to focus). In an embodiment, at least partially based on the determined distance, the controller 130*a* can determine the first or second focal length for the switchable lens (e.g., for the switchable lens 111*a* or for the switchable lens 111*b*) and can switch or direct switching of the switchable lens to the determined focal length.

Generally, the magnetic field source 50*b* can be any suitable magnet, which can establish any suitable magnetic field that can vary from one embodiment to the next. In the illustrated embodiment, the magnetic field source 50*b* is a dipole magnet, such as a permanent magnet (e.g., a ferromagnet). In an embodiment, the magnetic field source 50*b* can be a dipole electromagnet. In an embodiment, the magnetic field source 50*b* can generate a magnetic field having both a dipole and a non-dipole contribution. In such an embodiment, the non-dipole contributions generally weaken more with distance from the magnetic field source 50*b* than do the dipole contributions so that at a sufficient distance from the magnetic field source 50*b* (e.g., at the sensor location 140*a*), the dominant contribution is that of a magnetic dipole. In an embodiment, the electromagnet can be operably coupled to the controller 130*a* or to an additional controller (e.g., to a controller in the second switchable lens device 110*b*), which can turn on or off the electromagnet or can change an intensity of the magnetic field established or generated thereby. For example, the electromagnet can be pulsed in a manner that can distinguish or identify the magnetic field established thereby from other, interfering magnetic fields that can be present in the subject's environment. Moreover, based on the detection output from the first field sensor 140*a*, the controller 130*a* can distinguish the identifiable pulsed magnetic field from other magnetic fields.

Generally, as mentioned above, the first field sensor 140*a* can be any suitable sensor or multiple sensors, which can be sufficiently miniaturized for placement in the subject's eye (e.g., MEMS based sensors that can be embedded in or mounted on the first switchable lens device 110*a*). Examples of suitable sensors include Hall effect sensors, magnetoresistance sensors (e.g., AMR magnetometer, GMR magnetometer), induction coils, magneto-diodes, Lorentz force based sensors, Electron Tunneling based sensor, MEMS compass, etc. In any event, the first field sensor 140*a* can be or can include any suitable sensor or combination of sensors that can detect the change in the location or orientation of the identifiable magnetic field 50*b*.

In an embodiment, the first switchable lens device 110*a* can be positioned at a predetermined location or orientation relative to the first optical axis 60*a* of the first eye, and the second switchable lens device 110*b* or the identifiable magnetic field 50*b* or pole axis of the magnetic field source 150*b* can be oriented relative to the second optical axis 60*b* of the second eye at a predetermined pitch angle $\alpha$. Generally, the predetermined pitch angle can be any suitable angle, which can vary from one embodiment to the next. For example, the pitch angle $\alpha$ can be a non-parallel angle relative to the first or second optical axis 60*a*, 60*b*, an obtuse angle, or an acute angle. Moreover, as described below in more detail, the pitch angle can be 0°, such that a magnetic field component of the identifiable magnetic field 50*b* is substantially parallel to the second optical axis 60*b*.

Furthermore, the identifiable magnetic field 50*b* can be oriented such that the first field sensor 140*a* or the controller 130*a* can distinguish between in-tilt or convergence of the eyes (e.g., when the subject attempts to change focus on from a first object to a second object that is closer to the subject) from co-tilt of the eyes (e.g., when the subject tilts or pivots eyes to focus on an object located peripherally, such as to the left or to the right of the subject). For example, the identifiable magnetic field 50*b* can be oriented at about 45° relative to the second optical axis 60*b* (e.g., within less than 1° of the 45°, within less than 2° of the 45°, within less than 5° of the 45°).

It should be appreciated that the identifiable magnetic field 50*b* can have any suitable orientation relative to the second optical axis 60*b*. For example, the identifiable magnetic field 50*b* can be oriented relative to the second optical axis 60*b* such that convergence of the eyes results in an increased magnitude or changed direction of the magnetic field vector (e.g., Lorentz force vector), which can be distinguishable from the direction of the magnetic field vector sensed by the first field sensor 140*a* when the eyes co-tilt, as discussed below in more detail. In other words, the identifiable magnetic field 50*b* can be oriented such that the detection output received from the first field sensor 140*a* can be processed by the controller 130*a* to distinguish or identify the change in magnitude or direction of the Lorentz force vector of the identifiable magnetic field 50*b* in a manner that the controller 130*a* can distinguish convergence or in-tilt of the eyes from co-tilt.

It should be also appreciated that the first field sensor 140*a* of the first switchable lens device 110*a* can be configured to measure the strength and direction of the magnetic field, to measure the component of the magnetic field in a specific sensitivity direction, or to include multiple (collocated or not) magnetic sensors each of which is configured to measure separately directed components of the magnetic field. In an embodiment, the first field sensor 140*a* includes a sensor configured to measure a magnetic field component oriented at 0° relative to the first optical axis 60*a*. In an embodiment, the first field sensor 140*a* includes a sensor configured to measure a magnetic field component oriented at 90° relative to the first optical axis 60*a* (e.g., in the plane of the first switchable lens device 110*a*) directed to or away from the second switchable lens device 110*b*. The first field sensor 140*a* is mounted or embedded within the first switchable lens device 110*a* so that as the first eye tilts, changing the direction of first optical axis 60*a* and first switchable lens device 110*a*, the sensitivity direction of the first field sensor 140*a* also changes. Accordingly, the value of a specific directional component of magnetic field measured by the first field sensor 140*a* will change based on changes in the tilt of the first eye. It should be further appreciated, that the value of a specific directional component of magnetic field measured by the first field sensor 140*a* will also be changed by changes in the direction the magnetic field source 50*b*, and the accompanying changes in the field at the location of the first field sensor 140*a*. Since the magnetic field source 50*b* is implanted in the second eye (either directly, or indirectly via being mounted in the second switchable lens device 110*b*), then field values measured by the first field sensor 140*a* will change based on changes in the tilt of the second eye. Accordingly, field values measured by the first field sensor 140*a* will change based on changes in the tilt of both the first eye and the second eye.

It should be also appreciated that the second switchable lens device 110*b* can include multiple magnets that can establish multiple identifiable magnetic fields. Moreover, a single identifiable magnetic field oriented at an acute or obtuse angle relative to the second optic axis 60*b* can be represented by superpositioning two or more identifiable magnetic fields established by multiple magnets. Conversely, a single tilted identifiable magnetic field source (e.g., magnetic field source oriented at 45° relative to the second optic axis 60*b*) can be represented as two magnetic field sources: e.g., an in-plane field source $m_{\parallel}$ oriented parallel to the plane of the IOL (i.e., orthogonal to the optical axis 60*b*), and an out-of-plane field source $m_{\perp}$ oriented perpendicular to the plane of the IOL (i.e., along the optical axis 60*b*). The first field sensor 140*a* can be configured to measure magnetic field at a specified angle relative to the optical axis 60*a*.

In an embodiment, the controller 130*a* can determine change in vergence between the first and second eyes of the subject responsive to the signals received from the field sensor 140*a* and from the acceleration sensors 145*a* or 145*b*. For example, the controller 130*a* can make a first determination of whether movement of the eyes corresponds to a change in vergence or a tilt of the eyes based on the signals received from the acceleration sensors 145*a*, 145*b*, as described above. The controller 130*a* can make a second determination of whether movement of the eyes corresponds to a change in vergence or tilt of the eye based on the signals received from the field sensor 140*a*. In an embodiment, the controller 130*a* can make a third determination of the position or change in vergence by comparing the first determination to the second determination (e.g., when the first and second determinations indicate a change in vergence, the controller 130*a* can make the third determination that the movement of the eyes corresponds to a change in vergence). Moreover, the controller 130*a* determined the value of the change in vergence by comparing the first and second determined changes in the vergence (e.g., by taking an average of the first and second determined changes in the vergence). In an embodiment, the controller 130*a* can generate a switching signal based on the third determination (e.g., the controller 130*a* can switch or direct switching of the first or second lens 111*a*, 111*b* responsive to the third determination).

In an embodiment, the controller 130*a* can determine that the first determination of change in vergence (e.g., determination based on the signals received from the acceleration sensors 145*a*, 145*b*) is different than the second determination of change in version (e.g., determination based on the signals received from the field sensor). For example, the first determination can indicate that the subject's eyes are tilting, while the second determination can indicate that the subject's eye are converging or diverging, or vice versa. Hence, for example, the controller 130*a* can be configured to generate a third determination that corresponds to maintaining the optical settings (e.g., the focal length) of the first or second lens 111*a*, 111*b*.

As described above, the acceleration sensor(s) can be associated with the first or second eye of the subject by any number of suitable mechanisms. For example, the acceleration sensor can be mechanically connected to the switchable lens device. Additionally or alternatively, the acceleration sensor can be implanted in the first or second eye of the subject. Also, remote acceleration sensor (that can be placed externally to the first and second eye) can be included in a personal electronic device that can be on the subject, implanted under the skin of the subject, or included in any number of suitable devices sized and configured to be carried by the subject. Again, the remote acceleration sensor can be operably coupled to the controller 130*a* and can send one or more signals to the controller 130*a*.

Figure 6A:
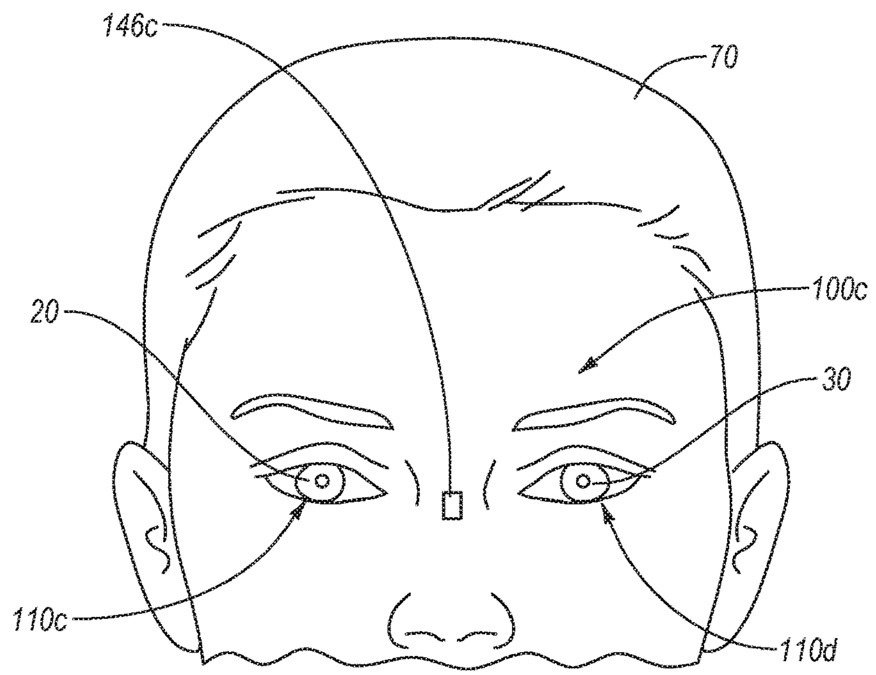
FIG. 6A is a schematic front view of a switchable lens system that includes two switchable lens devices oriented by the subject's eyes at a first vergence therebetween, according to yet another embodiment.
Figure 6B:
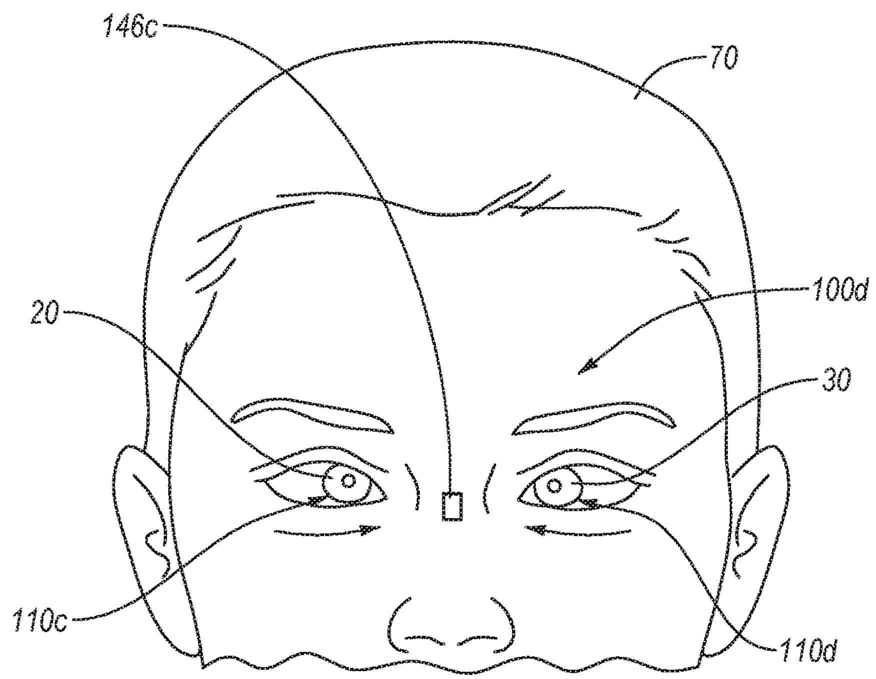
FIG. 6B is a schematic front view of the switchable lens system of FIG. 7A in which the switchable lens devices are oriented by the subject's eyes at a second vergence therebetween.

Moreover, the switchable lens device can include any number of suitable switchable lenses that can be associated with the first or second eye of the subject to provide corrective focusing for the corresponding eye of the subject. FIGS. 6A-6B illustrate a switchable lens systems 100*c*, 100*d* worn by subject 70. Specifically, the switchable lens system 100*c* includes switchable lens devices 110*c*, 110*d*. The switchable lens device 110*c* can include a first switchable contact lens that can be positioned in the first eye 20 of the subject 70, and the switchable lens device 110*d* can include a second switchable contact lens 110*d* that can be positioned in second eye 30 of the subject 70. Except as otherwise described herein, the switchable lens system 100*c* can be similar to or the same as any of the switchable lens systems described herein.

For example, the switchable lens system 100*c* can include one or more acceleration sensors that can be associated with the first eye 20 or second eye 30 and detect respective movements thereof, as described above. In an embodiment, the switchable lens system 100*c* can include an acceleration sensor 146*c*, that can be positioned remotely from the first eye 20 or second eye 30. Specifically, for example, the acceleration sensor 146*c* can be positioned on or mechanically connected to the head of the subject 70 (e.g., such as to detect movement of the subject 70 or movement of the subject's head).

In an embodiment, the acceleration sensor 146*c* can be operably coupled to the controller. For example, as described above, the controller can receive one or more signals from the acceleration sensor 146*c*. In some embodiments, the signals received from the acceleration sensor 146*c* can be processed or used by the controller to filter out noise from the acceleration sensors associated with the first eye 20 or with the second eye 30 and sensing the respective motion or acceleration thereof. In the illustrated embodiment, the acceleration sensor 146*c* is shown as positioned between the first and second eyes 20, 30 of the subject 70. For example, the acceleration sensor 146*c* can be implanted under the skin of the subject 70 (e.g., near the nose of the subject 70). It should be appreciated, however, that the acceleration sensor 146*c* can be located at any suitable location (e.g., as described above).

Also, as mentioned above, the controller or one or more portions thereof can be located at any number of suitable locations. For example, one or more portions of the controller can be included in a personal electronic device (e.g., the portable electronic device can include an acceleration sensor or can receive one or more signals from one or more acceleration sensors, such as from the acceleration sensor 146*a*). Moreover, the acceleration sensor 146*c* can be operably connected to the controller with any number of suitable connections (e.g., hardwired or wireless).

Figure 7:
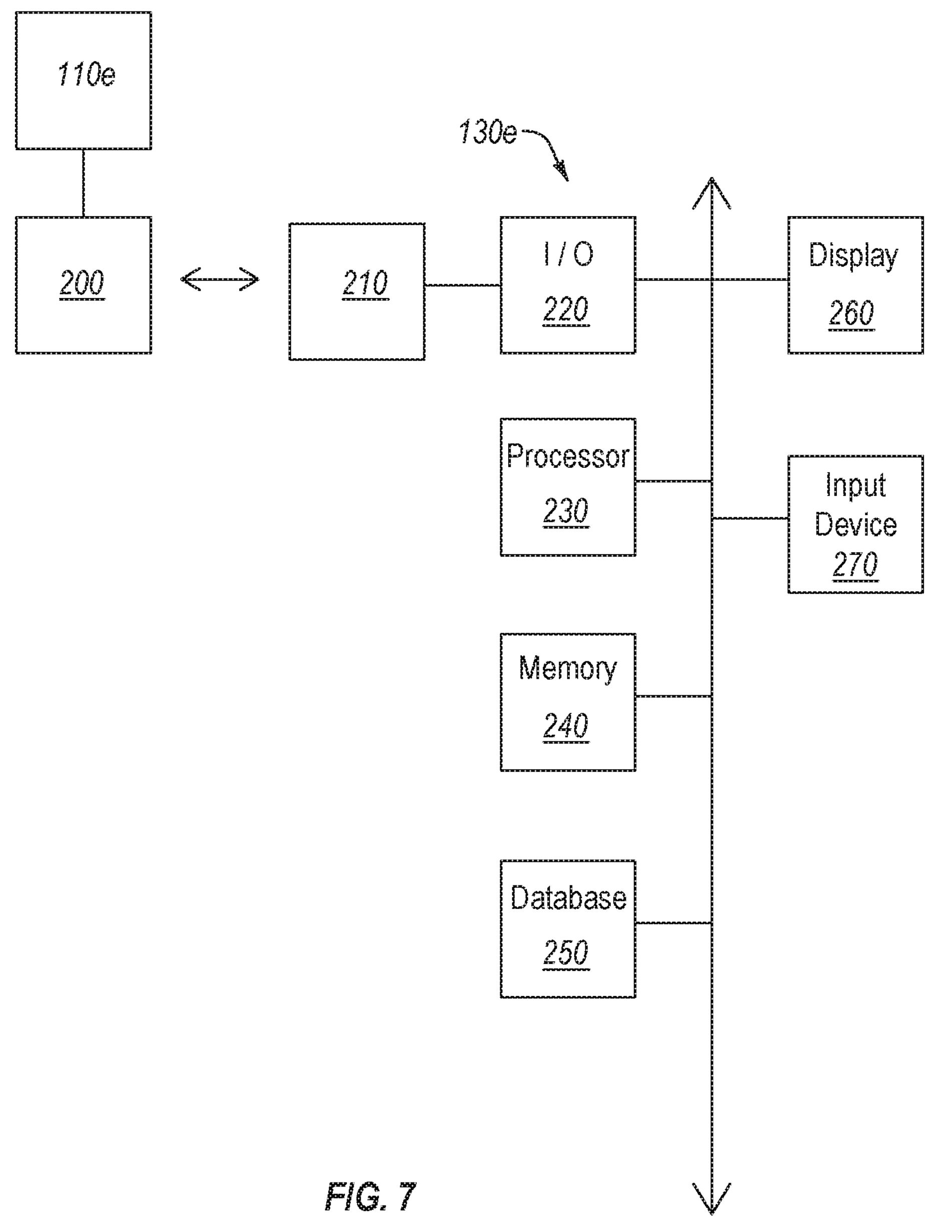
FIG. 7 is a block diagram of a switchable lens system, according to an embodiment.

In an embodiment, as shown in FIG. 7, a switchable lens device 110*e* can include or can be coupled to a communication device 200 (e.g., at least one receiver, transmitter, transceiver, or combinations thereof) that can receive data or instructions related to modification of the focal length(s) of one or more switchable lenses of the switchable lens device 110*e*. As described above, a switchable lens system can include the controller 130*e* (e.g., the controller 130*e* can receive one or more signals and can determine vergence rotation of the eye and/or suitable focal length for the switchable lenses of the switchable lens device 110*e*). In an embodiment, the controller 130*e* can include I/O interface 220, processor 230, and memory 240 operably coupled together. In an embodiment, the controller 130*e* can include a database 250 (e.g., the database 340 and can have data stored in a storage memory of the controller 130*e*). For example, the controller 130*e* can store one or more parameters in the database 340 (e.g., the controller 130*e* can store training or tuning data in the database 340).

In an embodiment, a communication device 210 (e.g., at least one receiver, transmitter, transceiver, or combinations thereof) can be operably coupled to the controller 130*e* and/or integrated therewith. For example, the communication device 210 can be operably coupled to the communication device 200 (e.g., via wired or wireless connection), such that the switchable lens device 110*e* and the controller 130*e* can transmit and receive data from one another. In an embodiment, display 260 and/or input device 270 (e.g., physical or virtual keyboard, microphone, etc.) can be operably coupled to the controller 130*e* and/or integrated therewith. For example, a user (e.g., a subject using and/or wearing the switchable lens device 110*e*) can enter input and/or data into the controller 130*e*, as described herein. Moreover, it should be appreciated that the controller 130*e* can be operably coupled to and/or incorporated with any number of suitable devices, such as personal electronic devices (e.g., personal computers, smart phones, tablets, etc.) and/or any other computing and/or input devices. It should be appreciated that any of the systems described herein (e.g., multi-focus lens systems, IOL systems, etc.) can have a similar or the same configuration as the system described above and illustrated in FIG. 7.

It will be understood that a wide range of hardware, software, firmware, or virtually any combination thereof can be used in the controllers described herein. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more programs running on one or more processors (e.g., as one or more programs running on one or more microprocessors), as firmware, or as virtually any combination thereof. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, the various embodiments described herein can be implemented, individually and/or collectively, by various types of electro-mechanical systems having a wide range of electrical components such as hardware, software, firmware, or virtually any combination thereof; and a wide range of components that can impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein can be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components can be referred to herein as "configured to." The reader will recognize that "configured to" or "adapted to" are synonymous and can generally encompass active-state components and/or inactive-state components and/or standby-state components, unless context requires otherwise.

While particular aspects of the present subject matter described herein have been shown and described, it will be apparent that, based upon the teachings herein, changes and modifications can be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, any recited operations therein can generally be performed in any order. Examples of such alternate orderings can include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A lens system, comprising:

a first acceleration sensor operably coupleable to a first eye of a subject;

a second acceleration sensor operably coupleable to a second eye of the subject;

at least one switchable lens device sized and configured to be placed in the first eye of the subject, the at least one switchable lens device including at least one switchable lens configured to selectively switch between a first focal length and at least a second focal length that is less than the first focal length responsive to one or more switching signals; and a controller operably coupled to the first acceleration sensor, the second acceleration sensor, and the at least one switchable lens device, the controller including control electrical circuitry configured to:

receive one or more first signals from the first acceleration sensor;

receive one or more second signals from the second acceleration sensor;

generate the one or more switching signals for switching the at least one switchable lens from the first focal length to the second focal length or from the second focal length to the first focal length responsive at least partially to the one or more first signals received from the first acceleration sensor and from the one or more second signals received from the second acceleration sensor; and differentiate at least one noise signal of the one or more first signals received from the first acceleration sensor from at least one detection signal of the one or more first signals received from the first acceleration sensor.

2. The lens system of claim 1, wherein the control electrical circuitry of the controller is configured to:

determine one or more of a velocity of the first eye, an acceleration of the first eye, a velocity of the second eye, or an acceleration of the second eye at least partially based on the one or more first signals received from the first acceleration sensor and the one or more second signals received from the second acceleration sensor; and generate the one or more switching signals responsive at least partially to the determined one or more of a velocity of the first eye, an acceleration of the first eye, a velocity of the second eye, or an acceleration of the second eye.

3. The lens system of claim 1, wherein the control electrical circuitry of the controller is configured to:

determine one or more of an angular velocity of the first eye, an angular acceleration of the first eye, an angular velocity of the second eye, or an angular acceleration of the second eye based on the one or more first signals received from the first acceleration sensor and the one or more second signals received from the second acceleration sensor; and generate the one or more switching signals responsive at least partially to one or more of the determined angular velocity of the first eye, the determined angular acceleration of the first eye, the determined angular velocity of the second eye, or the angular acceleration of the second eye.

4. The lens system of claim 1, wherein the control electrical circuitry of the controller is configured to:

determine one or more of a difference in angular position, a difference in angular velocity, or a difference in angular acceleration between the first eye and the second eye based on the one or more first signals received from the first acceleration sensor and the one or more second signals received from the second acceleration sensor; and generate the one or more switching signals responsive at least partially to one or more of the determined difference in angular position, the determined difference in angular velocity, or the determined difference in angular acceleration between the first eye and the second eye.

5. The lens system of claim 1, wherein the control electrical circuitry of the controller is configured to:

determine one or more of a change in the difference in angular position, a change in the difference in angular velocity, or a change in the difference in angular acceleration between the first eye and the second eye based on the one or more first signals received from the first acceleration sensor and the one or more second signals received from the second acceleration sensor; and generate the one or more switching signals responsive at least partially to one or more of the determined change in the difference in angular position, the determined change in the difference in angular velocity, or the determined change in the difference in angular acceleration between the first eye and the second eye.

6. The lens system of claim 1, wherein the control electrical circuitry of the controller is configured to determine convergence or divergence between the first eye and the second eye responsive to the at least partially to the one or more first signals received from the first acceleration sensor.

7. The lens system of claim 1, wherein at least a portion of the controller, which receives the one or more first signals from the first acceleration sensor, is located externally relative to the subject.

8. The lens system of claim 1, wherein at least a portion of the controller, which receives the one or more first signals from the first acceleration sensor, is wearable.

9. The lens system of claim 1, further including a portable computing device including at least a portion of the controller, the portable computing device configured to receive the one or more first signals from the first acceleration sensor.

10. The lens system of claim 1, wherein the controller is located remotely from the at least one switchable lens device.

11. The lens system of claim 1, wherein the controller is mechanically coupled to the at least one switchable lens device.

12. The lens system of claim 1, wherein the first acceleration sensor is operably coupled to the controller via at least one of a radio frequency connection, an optical transmission connection, an ultrasonic connection, or an electrical-conductor connection.

13. The lens system of claim 1, further including:

a magnetic field source sized and configured to be placed in the first eye of the subject or in a second eye of the subject, the magnetic field source configured to establish an identifiable magnetic field having a predetermined orientation relative to the first eye; and a sensor configured to detect a change in the established identifiable magnetic field corresponding to a vergence rotation between the first eye and the second eye, the sensor being configured to generate one or more detection outputs at least partially based on the detected change in the established magnetic field, the sensor being operably coupled to the controller.

14. The lens system of claim 13, wherein the control electrical circuitry of the controller is configured to generate the one or more switching signals responsive at least partially to one or more detection outputs at least partially based on the detected change in the established magnetic field.

15. The lens system of claim 14, wherein the control electrical circuitry of the controller is configured to:

determine convergence or divergence between the first eye and the second eye at least partially responsive to one or more of the velocity of the first eye or the acceleration of the first eye and at least partially based on the detected change in the established magnetic field; and generate the one or more switching signals responsive to the determined convergence or divergence between the first eye and the second eye.

16. The lens system of claim 1, wherein the first acceleration sensor is secured to a first switchable lens device of the at least one switchable lens device.

17. The lens system of claim 16, wherein the second acceleration sensor is secured to a second switchable lens device of the at least one switchable lens device.

18. The lens system of claim 1, where:

one or more of the first acceleration sensor includes a first plurality of accelerometers operably coupleable to the first eye or the second acceleration sensor includes a second plurality of accelerometers operably coupleable the second eye; and the control electrical circuitry of the controller is configured to at least one of determine angular motion of the first eye responsive to comparison of the signals from the first plurality of accelerometers or determine angular motion of the second eye responsive to comparison of comparing signals received from the second plurality of accelerometers.

19. The lens system of claim 1, wherein the control electrical circuitry is configured to differentiate the at least one noise signal and the at least one detection signal by comparing a magnitude of a first signal of the one or more first signals to a magnitude of a second signal of the one or more first signals and by identifying the first signal as the at least one noise signal, the first signal and the second signal being received from the first acceleration sensor.

20. The lens system of claim 19, wherein the control electrical circuitry of the controller is configured to generate the one or more switching signals by rejecting the at least one noise signal, the one or more switching signals being at least partially responsive to the at least one detection signal.

21. The lens system of claim 19, wherein the second signal corresponds to a lateral acceleration or motion, and the first signal corresponds to a non-lateral acceleration or motion.

22. The lens system of claim 19, wherein the second signal is associated with a converging movement of the first eye and a second eye or a diverging movement of the first eye and the second eye.

23. The lens system of claim 22, wherein the control electrical circuitry of the controller is configured to receive user input associating the second signal with a converging movement of the first eye and a second eye or a diverging movement of the first eye and the second eye.

24. The lens system of claim 22, wherein the control electrical circuitry of the controller is configured to receive user input associating the first signal with a lack of converging movement of the first eye and a second eye or a diverging movement of the first eye and the second eye.

25. The lens system of claim 24, wherein the control electrical circuitry of the controller is configured to receive user input associating the first signal with at least one of a head movement or body movement of the subject.

26. The lens system of claim 19, wherein the second signal has a shorter duration than the first signal.

27. The lens system of claim 26, wherein the duration of the second signal is less than 1 second.

28. The lens system of claim 19, wherein the second signal has a smaller magnitude than the first signal.

29. The lens system of claim 1, wherein the control electrical circuitry of the controller includes a signal filter that is configured to filter out the at least one noise signal from the one or more first signals from the first acceleration sensor and allow to pass the at least one detection signal of the one or more first signals from the first acceleration sensor, the at least one detection signal corresponding to a lateral acceleration or motion, and the at least one noise signal corresponds to a non-lateral acceleration or motion.

30. The lens system of claim 29, wherein the control electrical circuitry of the controller is operably coupled to the signal filter and receives the at least one detection signal that passes the signal filter.

31. The lens system of claim 1, wherein the control electrical circuitry of the controller includes a signal filter that is configured to filter out the at least one noise signal from the one or more first signals from the first acceleration sensor and allow to pass the at least one detection signal from the one or more first signals from the first acceleration sensor, the at least one detection signal has a shorter duration than the at least one noise signal.

32. The lens system of claim 31, wherein the control electrical circuitry of the controller is operably coupled to the signal filter and receives that at least one detection signal that passes the signal filter.

33. The lens system of claim 1, further including an intraocular device that includes the at least one switchable lens device.

34. The lens system of claim 1, further including a contact lens that includes the at least one switchable lens device.

35. The lens system of claim 1, further including one or more physiological sensors positionable and configured to detect one or more physiological characteristics of the subject, the one or more physiological sensors operably coupled to electronic circuitry of the controller, and the control electrical circuitry configured to generate the one or more switching signals for switching the at least one switchable lens from the first focal length to the second focal length or from the second focal length to the first focal length responsive at least partially to one or more signals received from the one or more physiological sensors.

36. The lens system of claim 35, wherein the one or more physiological sensors include one or more of a glucose sensor, an electrolyte sensor, a heart rate sensor, a pulse sensor, an oxygen sensor, a temperature sensor, or a moisture sensor.

37. A lens system, comprising:

a first acceleration sensor operably coupleable to a first eye of a subject;

a second acceleration sensor operably coupleable to a second eye of a subject;

a third acceleration sensor positionable externally of the first eye of the subject and of the second eye of the subject and locatable on the subject;

at least one switchable lens device sized and configured to be placed in the first eye of the subject, the at least one switchable lens device including at least one switchable lens configured to selectively switch between a first focal length and at least a second focal length that is less than the first focal length responsive to one or more switching signals; and a controller operably coupled to the first acceleration sensor, the second acceleration sensor, the third acceleration sensor, and the at least one switchable lens device, the controller including control electrical circuitry configured to:

receive one or more signals from the first acceleration sensor;

receive one or more signals from the second acceleration sensor;

receive one or more signals from the third acceleration sensor;

generate the one or more switching signals for switching the at least one switchable lens from the first focal length to the second focal length or from the second focal length to the first focal length responsive at least partially to the one or more signals received from the first acceleration sensor, the second acceleration sensor, and the third acceleration sensor; and differentiate at least one noise signal of the one or more first signals received from the first acceleration sensor from at least one detection signal of the one or more first signals received from the first acceleration sensor.

38. The lens system of claim 37, further including:

a magnetic field source sized and configured to be placed in the first eye of the subject or in the second eye, the magnetic field source configured to establish an identifiable magnetic field having a predetermined orientation relative to the first eye; and a sensor configured to detect a change in the established identifiable magnetic field corresponding to a vergence rotation between the first eye and the second eye, the sensor being configured to generate one or more detection outputs at least partially based on the detected change in the established magnetic field, the sensor being operably coupled to the controller.

39. The lens system of claim 38, wherein the control electrical circuitry of the controller is configured to generate the one or more switching signals responsive at least partially to one or more detection outputs at least partially based on the detected change in the established magnetic field.

40. The lens system of claim 38, wherein the control electrical circuitry of the controller is configured to:

determine convergence or divergence between the first eye and the second eye at least partially responsive to one or more of the velocity of the first eye or the acceleration of the first eye and at least partially based on the detected change in the established magnetic field; and generate the one or more switching signals responsive to the determined convergence or divergence between the first eye and the second eye.

41. The lens system of claim 37, wherein the control electrical circuitry of the controller is configured to differentiate the at least one noise signal of the one or more signals received from the first acceleration sensor from the at least one detection signal of the one or more signals received from the first acceleration sensor by comparing a magnitude of a first signal of the one or more signals to a magnitude of a second signal of the one or more signals and by identifying the first signal as the noise signal, the first signal and the second signal being received from the first acceleration sensor.

42. The lens system of claim 41, wherein the control electrical circuitry of the controller is configured to generate the one or more switching signals by rejecting the at least one noise signal, the one or more switching signals being at least partially responsive to the at least one detection signal.

43. The lens system of claim 41, wherein the control electrical circuitry of the controller is configured to differentiate the at least one noise signal of the one or more signals received from the first acceleration sensor from the at least one detection signal of the one or more signals received from the first acceleration sensor by comparing a magnitude of a first signal of the one or more signals to a magnitude of a third signal received from the third acceleration sensor and by identifying the first signal as the noise signal.

44. The lens system of claim 37, further including one or more physiological sensors positionable and configured to detect one or more physiological characteristics of the subject, the one or more physiological sensors being operably coupled to electronic circuitry of the controller, and the electrical circuitry being configured to generate the one or more switching signals for switching the at least one switchable lens from the first focal length to the second focal length or from the second focal length to the first focal length responsive at least partially to one or more signals received from the one or more physiological sensors.

45. The lens system of claim 44, wherein the one or more physiological sensors include one or more of a glucose sensor, an electrolyte sensor, a heart rate sensor, a pulse sensor, an oxygen sensor, a temperature sensor, or a moisture sensor.

* * * * *